United States Patent
Shindou et al.

(10) Patent No.: US 10,705,227 B2
(45) Date of Patent: Jul. 7, 2020

(54) SCINTILLATOR PANEL

(71) Applicant: KONICA MINOLTA, INC., Tokyo (JP)

(72) Inventors: Hiromichi Shindou, Hachioji (JP); Kiyoshi Hagiwara, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/386,720

(22) Filed: Apr. 17, 2019

(65) Prior Publication Data

US 2019/0324158 A1    Oct. 24, 2019

(30) Foreign Application Priority Data

Apr. 19, 2018   (JP) ................................ 2018-080586

(51) Int. Cl.
    *G01T 1/20*    (2006.01)
    *A61B 6/00*    (2006.01)

(52) U.S. Cl.
    CPC .......... *G01T 1/2002* (2013.01); *A61B 6/4208* (2013.01); *G01T 1/2018* (2013.01)

(58) Field of Classification Search
    CPC ..... A61B 6/4208; A61B 6/484; G01T 1/2002; G01T 1/2018
    See application file for complete search history.

(56) References Cited

U.S. PATENT DOCUMENTS 5,519,227 A * 5/1996 Karellas ................. G01T 1/202
                                                  250/370.11

FOREIGN PATENT DOCUMENTS

| WO | 2014069284 A1 | 5/2014 | |
| WO | 2014080941 A1 | 5/2014 | |
| WO | WO-2014080941 A1 * | 5/2014 | ........... G01T 1/2002 |

* cited by examiner

*Primary Examiner* — Mark R Gaworecki
(74) *Attorney, Agent, or Firm* — Cantor Colburn LLP

(57) ABSTRACT

[Problem] Provided is a layered structure in which a non-scintillator layer is utilized as a light transmission path to a sensor so as to transmit light in a vertical direction through the non-scintillator layer without allowing the light to re-enter a scintillator layer.
[Means for Solution] Provided is a scintillator panel having a structure in which a scintillator layer and a non-scintillator layer are repeatedly arranged in a direction substantially parallel to a radiation incident direction. In this scintillator panel, the scintillator layer contains at least a phosphor, a binder resin, and voids; the non-scintillator layer is radiolucent; the scintillator layer and the non-scintillator layer have an irregular structure at their interface; and an arithmetic surface roughness Ra attributed to irregularities is $\frac{1}{400}$ to $\frac{1}{10}$ of the width of the non-scintillator layer.

4 Claims, 5 Drawing Sheets

Definition of Surface Roughness

Definition of Gaps between Transparent Fine Particles

SCINTILLATOR PANEL

CROSS REFERENCE TO RELATED APPLICATION

The present application claims priority under 35 U.S.C. § 119 to Japanese patent application No. 2018-80586 filed on Apr. 19, 2018, the entirety of which is incorporated herein by references.

TECHNOLOGICAL FIELD

The present invention relates to a novel scintillator panel suitable for Talbot system.

BACKGROUND

Currently, in X-ray image diagnosis, an absorption image capturing attenuation of an X-ray after transmission through an object is used. Meanwhile, X-rays are one type of electromagnetic waves; therefore, in recent years, attention has been given to their wave nature, and attempts have been made to produce an image of a phase shift of an X-ray after transmission through an object. Such attenuation and phase shift are referred to as "absorption contrast" and "phase contrast", respectively. An imaging technology utilizing this phase contrast has a higher sensitivity to light elements than a conventional technology utilizing absorption contrast and is thus believed to be highly sensitive to human soft tissues containing a large amount of light elements.

However, a conventional phase contrast imaging technology requires the use of a synchrotron X-ray source and a microfocus X-ray tube, and the former entails a large-scale facility while the latter cannot secure an X-ray dose sufficient for photographing a human body; therefore, it has been considered difficult to put such a conventional phase contrast imaging technology to practical use at general medical facilities.

In order to solve these problems, X-ray image diagnosis (Talbot system) which employs an X-ray Talbot-Lau interferometer that is capable of acquiring a phase contrast image with the use of an X-ray source conventionally used in medical practice is expected.

As illustrated in FIG. 5, a Talbot-Lau interferometer has a G0 lattice, a G1 lattice and a G2 lattice that are each arranged between a medical X-ray tube and an FPD, and visualizes refraction of an X-ray caused by a subject as moiré fringes. An X-ray is irradiated in a longitudinal direction from an X-ray source arranged in an upper part, and the X-ray reaches an image detector through the G0 lattice, the subject, the G1 lattice, and the G2 lattice.

As a method of producing a lattice, for example, a method in which a silicon wafer having high X-ray transparency is etched to form lattice-form recesses and these recesses are subsequently filled with a heavy metal having excellent X-ray shielding properties is known.

However, in this method, it is difficult to increase the area due to, for example, the size of available silicon wafer and restrictions on an etching device, and the imaging subject is thus limited to a small part. In addition, since not only it is not easy to form deep recesses on a silicon wafer by etching but also it is hard to evenly fill a metal into deep parts of the recesses, it is difficult to produce a lattice having a thickness enough to sufficiently shield X-rays. For this reason, particularly under high-voltage photographing conditions, a favorable image cannot be obtained due to transmission of X-rays through a lattice.

In view of the above, the scintillators, which are scintillators imparted with a lattice function and emit light in a slit form, are drawing attention.

For example, Patent Document 1 discloses a radiation detection device in which a substrate having partition walls formed on its surface and a photodetector face with each other, wherein cells divided by the partition walls are formed in a space between the substrate and the photodetector, the cells are filled with a phosphor, light-detecting pixels are arranged on the surface of the photodetector that is not in contact with the partition walls, and an adhesive layer is formed between the partition walls and the phosphor, and the photodetector. In Patent Document 1, it is disclosed that the radiation detection device satisfies a relationship of $\lambda 2 \geq \lambda 1 \geq \lambda 3$, wherein $\lambda 1$, $\lambda 2$ and $\lambda 3$ represent the average refractive index of the phosphor, that of the light-detecting pixels and that of the adhesive layer, respectively.

Further, Patent Document 2 discloses a scintillator panel including: a plate-form substrate; partition walls arranged on the substrate; and a scintillator layer filled in cells divided by the partition walls, wherein the partition walls are constituted by a material containing a low-melting-point glass as a main component and the scintillator layer is composed of a phosphor and a binder resin. In Patent Document 2, it is disclosed that the refractive index Np of the phosphor and the refractive index Nb of the binder resin satisfy a relationship of $-0.3<Np-Nb<0.8$, i.e., these refractive index values are close to each other.

In Patent Documents 1 and 2, however, no attention is given to the effective use of the partition walls as a light transmission path.

DESCRIPTION OF THE RELATED ART

Patent Document 1: WO 2014/069284
Patent Document 2: WO 2014/080941

SUMMARY

An object of the present invention is to provide a layered structure in which a non-scintillator layer is utilized as a light transmission path to a sensor so as to transmit light in a vertical direction through the non-scintillator layer without allowing the light to re-enter a scintillator layer.

To achieve the abovementioned object, an image forming apparatus reflecting one aspect of the present invention contains:

a scintillator panel having a structure in which a scintillator layer and a non-scintillator layer are repeatedly arranged in a direction substantially parallel to a radiation incident direction, wherein the scintillator layer contains at least a phosphor, a binder resin, and voids, the non-scintillator layer is radiolucent, the boundary interface between the scintillator layer and the non-scintillator layer have an irregular structure, and an arithmetic surface roughness Ra attributed to irregularities is $\frac{1}{400}$ to $\frac{1}{10}$ of the width of the non-scintillator layer.

To achieve at least one of the abovementioned objects, an image forming apparatus reflecting another aspect of the present invention contains:

a scintillator panel having a structure in which a scintillator layer and a non-scintillator layer are repeatedly arranged in a direction substantially parallel to a radiation incident direction, wherein the scintillator layer contains at least a phosphor, a binder resin, and voids, the non-scintillator layer is radiolucent and contains transparent fine particles, and the translucent fine particles exist such that their average gap is ¹⁄₁₀ to four times of the width of the non-scintillator layer.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

The scintillator panel of the present invention will now be described.

Figure 1:
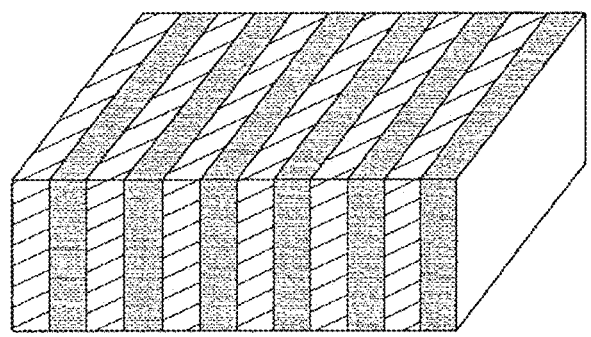
FIG. 1 is a schematic view illustrating one mode of the scintillator panel according to the present invention.
Figure 2:
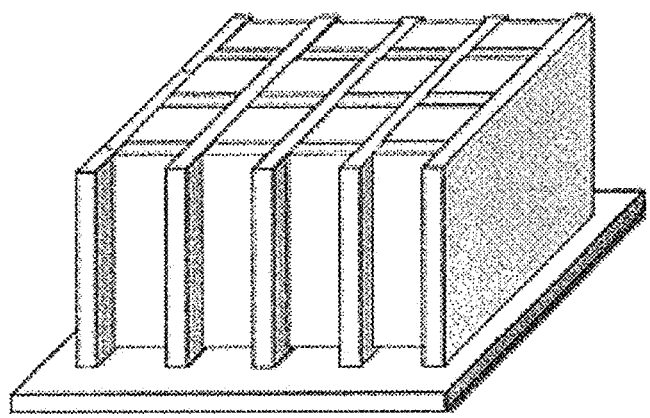
FIG. 2 is a schematic view illustrating another mode of the scintillator panel according to the present invention.

As illustrated in FIG. 1 and FIG. 2, the scintillator panel of the present invention has a structure in which a scintillator layer having a function of emitting light upon receiving an X-ray and a non-scintillator layer are repeatedly laminated in a direction substantially parallel to a radiation incident direction. The light emitted by the scintillator layer as induced by radiation can be converted into an electrical signal through a detector, whereby a digital image can be obtained.

In the present invention, as one mode of the scintillator panel illustrated in FIG. 1, a lattice-type scintillator having a structure in which a scintillator layer and a non-scintillator layer are repeatedly laminated in a direction substantially parallel to a radiation incident direction can be employed. The term "substantially parallel" used herein means almost parallel, and the scope of the term "substantially parallel" also encompasses being completely parallel as well as being parallel with some inclination or curvature. Such a lattice-type scintillator can have an increased area. It is noted here that a state of being "substantially parallel" may be hereinafter simply referred to as "parallel".

Further, as another mode of the scintillator panel of the present invention, a scintillator having the segmented structure illustrated in FIG. 2 can be adopted. Specifically, this scintillator includes: a radiolucent plate-form substrate; a radiolucent partition wall structure part that is arranged on the substrate and has lattice-shaped unit segments; and a scintillator layer formed by filling the lattice-shaped unit segments with a phosphor.

In the segmented scintillator, the scintillator layer and plural partition walls that are juxtaposed at a prescribed pitch constitute a photoelectric conversion element. Two or more segmented scintillator layers may be adhered via an interlayer adhesive material such that their partition walls abut with each other. The scintillator layers constituting such a segmented structure extend uniformly and planarly over the substrate and may be integrated together, or plural small-sized scintillator layers may be tiled on the substrate.

Light emitted from a scintillator layer due to X-ray irradiation is transmitted to a sensor; however, the light emitted from the scintillator layer passes through a non-scintillator layer and may thus re-enter other adjacent scintillator layer. Since the re-entering light is refracted or scattered in the scintillator layer, the amount of light reaching the sensor in a vertical direction is consequently reduced as a whole, and this causes a reduction in brightness and MTF. Therefore, it is necessary to guide the light entering the non-scintillator layer to the sensor without allowing the light to enter the scintillator layer, and it is critical to allow the light to be transmitted to the sensor in a vertical direction for suppressing the image blurriness and improving the brightness and the MTF.

Scintillator Layer

The scintillator layer in the present invention is a layer containing a scintillator as a main component and contains at least a phosphor, a binder resin, and voids.

As the phosphor, a substance capable of converting radiation, such as an X-ray, into light having a different wavelength, such as visible light, can be used as appropriate. Specifically, for example, those scintillators and phosphors that are described on pages 284 to 299 of "Phosphor Handbook" (edited by Phosphor Research Society, Ohmsha Ltd., 1987) and the substances listed on the website "Scintillation Properties (http://scintillator.lbl.gov/)" of the US Lawrence Berkeley National Laboratory are considered, and even a substance that is not mentioned therein can be used the scintillator as long as it is a "substance capable of converting radiation, such as an X-ray, into light having a different wavelength" can be used as the scintillator.

Specific examples of the composition of the scintillator include the followings. First, metal halide phosphors represented by the following basic composition formula (I) can be mentioned:

$$M_I X \cdot a M_{II} X'_2 \cdot b M_{III} X''_3 : zA \qquad (I)$$

In the above basic composition formula (I), $M_I$ represents at least one selected from the group consisting of elements that can be monovalent cations, i.e., lithium (Li), sodium (Na), potassium (K), rubidium (Rb), cesium (Cs), thallium (Tl), and silver (Ag).

$M_{II}$ represents at least one selected from the group consisting of elements that can be divalent cations, i.e., beryllium (Be), magnesium (Mg), calcium (Ca), strontium (Sr), barium (Ba), nickel (Ni), copper (Cu), zinc (Zn), and cadmium (Cd).

$M_{III}$ represents at least one selected from the group consisting of scandium (Sc), yttrium (Y), aluminum (Al), gallium (Ga), indium (In), and elements belonging to lanthanoid. X, X' and X" each represent a halogen element and may be different elements or the same element.

A represents at least one element selected from the group consisting of Y, Ce, Pr, Nd, Sm, Eu, Gd, Tb, Dy, Ho, Er, Tm, Yb, Lu, Na, Mg, Cu, Ag, Tl, and Bi (bismuth).

Further, a, b and z each independently represent a numerical value in the respective ranges of $0 \leq a < 0.5$, $0 \leq b < 0.5$, and $0 < z < 1.0$.

Rare earth-activated metal fluorohalide phosphors represented by the following basic composition formula (II) can be mentioned as well:

$$M_{II}FX:zLn \qquad (II)$$

In the above basic composition formula (II), $M_{II}$ represents at least one alkaline earth metal element, Ln represents at least one element belonging to lanthanoid, X represents at least one halogen element, and z satisfies $0 < z \leq 0.2$.

In addition, rare earth oxysulfide phosphors represented by the following basic composition formula (III) can be mentioned:

$$Ln_2O_2S:zA \qquad (III)$$

In the above basic composition formula (III), Ln represents at least one element belonging to lanthanoid, A represents at least one element selected from the group consisting of Y, Ce, Pr, Nd, Sm, Eu, Gd, Tb, Dy, Ho, Er, Tm, Yb, Lu, Na, Mg, Cu, Ag, Tl and Bi, and z satisfies $0 < z < 1$.

Particularly, $Gd_2O_2S$ using gadolinium (Gd) as Ln is preferred since it is known to exhibit high emission characteristics in a wavelength region where the sensor panel is most likely to receive light when, for example, terbium (Tb) or dysprosium (Dy) is used as the element species of A.

Further, metal sulfide phosphors represented by the following basic composition formula (IV) can be mentioned:

$$M_{II}S:zA \qquad (IV)$$

In the above basic composition formula (IV), $M_{II}$ represents at least one selected from the group consisting of elements that can be divalent cations, i.e., alkaline earth metals, Zn, Sr and Ga, A represents at least one element selected from the group consisting of Y, Ce, Pr, Nd, Sm, Eu, Gd, Tb, Dy, Ho, Er, Tm, Yb, Lu, Na, Mg, Cu, Ag, Tl and Bi, and z satisfies $0 < z < 1$.

Still further, metal oxoacid salt phosphors represented by the following basic composition formula (V) can be mentioned:

$$M_{IIa}(AG)_b:zA$$

In the above basic composition formula (V), $M_{II}$ represents a metal element that can be a cation, (AG) represents at least one oxoacid group selected from the group consisting of phosphates, borates, silicates, sulfates, tungstates and aluminates, and A represents at least one element selected from the group consisting of Y, Ce, Pr, Nd, Sm, Eu, Gd, Tb, Dy, Ho, Er, Tm, Yb, Lu, Na, Mg, Cu, Ag, Tl, and Bi.

Further, a and b each represent any value that can be taken in accordance with the valence of the metal and that of the oxoacid group, and z satisfies $0 < z < 1$.

Moreover, metal oxide phosphors represented by the following basic composition formula (VI) can be mentioned:

$$M_aO_b:zA \qquad (VI)$$

In the above basic composition formula (VI), M represents at least one selected from metal elements that can be cations.

A represents at least one element selected from the group consisting of Y, Ce, Pr, Nd, Sm, Eu, Gd, Tb, Dy, Ho, Er, Tm, Yb, Lu, Na, Mg, Cu, Ag, Tl, and Bi.

Further, a and b each represent any value that can be taken in accordance with the valence of the metal and that of oxoacid group, and z satisfies $0 < z < 1$.

In addition to the above, metal acid halide phosphors represented by the following basic composition formula (VII) can be mentioned:

$$LnOX:zA \qquad (VII)$$

In the above basic composition formula (VII), Ln represents at least one element belonging to lanthanoid, X represents at least one halogen element, and A represents at least one element selected from the group consisting of Y, Ce, Pr, Nd, Sm, Eu, Gd, Tb, Dy, Ho, Er, Tm, Yb, Lu, Na, Mg, Cu, Ag (silver), Tl and Bi (bismuth), and z satisfies $0 < z < 1$.

The phosphor is contained as scintillator particles, and the average particle size thereof is selected in accordance with the thickness of the scintillator layer in the lamination direction. The average particle size is usually the same or less, i.e., 100% or less, preferably 90% or less, with respect to the thickness of the scintillator layer in the lamination direction; however, since the average particle size relates to the desired irregularities of the interface between the scintillator layer and the non-scintillator layer, it may be larger than the thickness of the scintillator layer and is selected as appropriate in accordance with the desired irregularities of the interface between the scintillator layer and the non-scintillator layer.

The content of the scintillator particles in the scintillator layer is preferably not less than 30% by volume, more preferably not less than 50% by volume, still more preferably not less than 70% by volume, taking into consideration the emission characteristics.

When the content of the scintillator particles is higher than this range, the filling rate of the scintillator decreases, and the brightness may thus be reduced.

The binder contained in the scintillator layer is preferably a material transparent to the emission wavelength of the scintillator so as not to inhibit the propagation of emitted light.

The binder is not particularly restricted as long as it does not adversely affect the object of the present invention, and examples thereof include natural polymeric substances, such as proteins including gelatin, polysaccharides including dextran, and gum Arabic; and synthetic polymeric substances, such as polyvinyl butyrals, polyvinyl acetates, nitrocellulose, ethylcellulose, vinylidene chloride-vinyl chloride copolymers, poly(meth)acrylates, vinyl chloride-vinyl acetate copolymers, polyurethanes, cellulose acetate butyrate, polyvinyl alcohols, polyesters, epoxy resins, polyolefin resins, and polyamide resins. These resins may be cross-linked using a crosslinking agent such as an epoxy or an isocyanate, and these adhesive resins may be used singly or in combination of two or more thereof. The binder may be a thermoplastic resin or a thermosetting resin.

The content of the binder in the scintillator layer is preferably 1 to 70% by volume, more preferably 5 to 50% by volume, still more preferably 10 to 30% by volume. When the content is lower than the lower limit value of this range, sufficient adhesiveness cannot be attained, whereas when the content is higher than the upper limit value of this range, the amount of emitted light may be reduced due to insufficient scintillator content.

The voids inside the scintillator layer preferably have a porosity in a range of higher than 0 but 30% by volume or lower. When the porosity is higher than this range, the filling rate of the scintillator decreases, and the brightness may thus be reduced. It is noted here that the voids are usually filled with air.

As means for forming voids inside the scintillator layer, for example, in the process of preparing the scintillator layer, air bubbles may be incorporated into the scintillator layer, or hollow polymer particles may be added. As means for providing irregularities on a surface of the scintillator layer or the non-scintillator layer, for example, an irregularity-forming treatment such as a blast treatment or an emboss treatment may be performed on the layer surface.

Usually, light is scattered by irregularities and voids, and this may prevent from the light from reaching a detector.

On the other hand, by satisfying the below-prescribed mode, light is refracted at the interface between the scintillator layer and the non-scintillator layer and efficiently taken into the non-scintillator layer. It is noted here that the average refractive index n1 of the binder resin and the voids of the scintillator layer can be calculated from the composition ratio of the binder resin and the voids (filled with air).

Non-Scintillator Layer

The non-scintillator layer in the present invention is a layer that does not contain a scintillator as a main component, and the content of a scintillator in the non-scintillator layer is less than 10% by volume, preferably less than 1% by volume, most preferably 0% by volume.

The non-scintillator layer is transparent. Therefore, the non-scintillator layer desirably contains, for example, a glass(es), a polymer material(es), and/or a metal(s) as a main component(s). These materials may be used singly, or in combination of two or more thereof in the form of a complex. In the case of the lattice-type scintillator illustrated in FIG. 1, the non-scintillator layer has a structure of being repeatedly laminated in a direction substantially parallel to a radiation incident direction and, in the case of the segmented scintillator illustrated in FIG. 2, the partition wall structure having lattice-shaped segments corresponds to the non-scintillator layer.

As the non-scintillator layer, specifically, one constituted by a material selected from the followings can be employed:

glasses, such as quartz, a borosilicate glass, and a chemically reinforced glass;

ceramics, such as sapphire, silicon nitride, and silicon carbide;

semiconductors, such as silicon, germanium, gallium arsenide, gallium phosphide, and gallium nitride;

polymers, for example, polyester such as polyethylene terephthalate (PET) and polyethylene naphthalate (PEN), aliphatic polyamides such as nylon, aromatic polyamides (aramid), polyimides, polyamide imides, polyether imides, polyethylenes, polypropylenes, polycarbonates, triacetates, cellulose acetate, epoxy, bismaleimide, polylactic acids, sulfur-containing polymers such as polyphenylene sulfides and polyether sulfones, polyether ether ketones, fluororesins, acrylic resins, and polyurethanes;

carbon fibers and glass fibers (particularly, fiber-reinforced resin sheets containing such fibers);

metals, such as aluminum, iron, and copper; and bionanofibers containing chitosan or cellulose.

From the standpoint of the ease of handling in the production, the non-scintillator layer is preferably constituted by a polymer.

Further, in a mode of containing the below-described particles, the non-scintillator layer contains transparent fine particles.

Examples of the transparent fine particles include organic particles, such as methyl polymethacrylate/acrylate-based resin fine particles, acrylic styrene-based resin fine particles, polymethyl methacrylate resin fine particles, silicon-based resin fine particles, polystyrene-based resin fine particles, polycarbonate resin fine particles, benzoguanamine-based resin fine particles, melamine-based resin fine particles, polyolefin-based resin fine particles, polyester-based resin fine particles, polyamide-based resin fine particles, and polyimide-based resin fine particles; inorganic particles of silica, zirconia, titania, and alumina; and metal fine particles.

The transparency to the non-scintillator layer may be given by not only adjusting the refractive index values of materials but also containing a transparent fine particle. For example, transparent fine particles and a non-scintillator layer-constituting material which have similar refractive index values may be used, or fine particles composed of a material having a high refractive index may be dispersed as transparent fine particles in a material constituting the non-scintillator layer. The transparent fine particles can have any average particle size that is smaller than the thickness of the non-scintillator layer. The amount of the transparent fine particles to be contained is selected such that the transparent fine particles have the below-prescribed average gap.

Among the above-described particles, in the present invention, it is preferred to use silica as the transparent fine particles and to form the non-scintillator layer by dispersing the transparent fine particles in a polymer. A dispersion method is not particularly restricted and, after melting the polymer or dissolving the polymer in a solvent, the transparent fine particles are dispersed in the resultant by mixing and the solvent may be subsequently removed as required.

The content ratio of the transparent fine particles is not particularly restricted as long as the below-described mode is satisfied.

In the present invention, it is preferred that a relationship of n1<n2 be satisfied when the average refractive index of the binder resin and the voids of the scintillator layer and the refractive index of the non-scintillator layer are defined as n1 and n2, respectively. By satisfying this relationship, light entering the non-scintillator layer is reflected at the interface and thereby allowed to pass through the non-scintillator layer without entering the scintillator layer, so that the non-scintillator layer can be utilized as a light transmission path.

Further, examples of particles in the non-scintillator layer include inorganic oxide particles, inorganic nitride particles, and particles of, for example, metal carbonates, metal sulfates, and metal chlorides. For example, a white pigment such as $TiO_2$ (anatase-type or rutile-type), MgO, $PbCO_3.Pb(OH)_2$, $BaSO_4$, $Al_2O_3$, M(II)FX (wherein, M(II) represents at least one atom selected from Ba, Sr and Ca, and X represents a Cl atom or a Br atom), $CaCO_3$, ZnO, $Sb_2O_3$, $SiO_2$, $ZrO_2$, lithopone [$BaSO_4$—ZnS], magnesium silicate, basic silisulfate, basic lead phosphate, or aluminum silicate can be used. Moreover, as nanoparticles, for example, glass beads, resin beads, hollow particles each having a hollow part therein, multi-hollow particles each having a large number of hollow parts therein, or porous particles can be used. These substances may be used singly, or in combination of two or more thereof.

In the present invention, the scintillator layer and/or the non-scintillator layer may satisfy either or both of the below-described modes.

Mode of Irregularities

Figure 3:
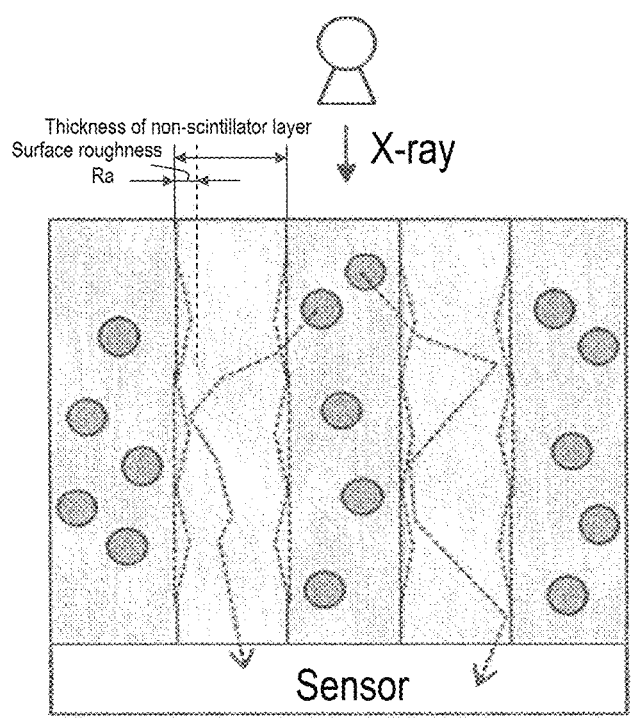
FIG. 3 is a schematic view illustrating the definition of the surface roughness of a scintillator layer interface according to the present invention.

FIG. 3 illustrates a mode of irregularities. The scintillator layer and the non-scintillator layer have an irregular structure at their interface, and the arithmetic average roughness Ra attributed to irregularities is $1/400$ to $1/10$, preferably $1/20$ to 1/10, of the width of the non-scintillator layer. When the arithmetic average roughness Ra is in this range, light entering the non-scintillator layer is reflected at the interface and thereby allowed to pass through the non-scintillator layer without entering the scintillator layer, so that the non-scintillator layer can be utilized as a light transmission path.

The arithmetic average roughness Ra is a value expressed in micrometers (m), which value is obtained by observing a cross-section prepared by means of, for example, cutting to determine a roughness curve and, as in an ordinary calculation method, extracting a portion that has a reference length L from the roughness curve toward its average line and subsequently taking an average of absolute values of deviation from the average line to the measured curve in the thus extracted portion. Alternatively, the Ra may be determined by directly measuring the respective surfaces of the scintillator layer and the non-scintillator layer prior to integration thereof or after disintegration thereof, using an ordinary surface roughness measuring instrument. Further, the thickness of the non-scintillator layer is defined as the shortest distance between reference lines each delineating a part that excludes the irregularities of the scintillator layer and has the smallest irregularity.

The irregularities have substantially the same function regardless of whether they are formed on the surface of the scintillator layer or the surface of the non-scintillator layer. As means for arranging such a mode of irregularities, for example, an irregularity-forming treatment such as a blast treatment or an emboss treatment may be performed on the layer surface. Alternatively, irregularities can also be formed by adjusting the formulation of the composition constituting the scintillator layer as described above.

The irregularities can be evaluated by cross-sectional SEM observation, or by dissolving away only the scintillator layer and measuring the surface roughness of the non-scintillator layer. The size of the irregularities can be arbitrarily adjusted by controlling the particle size and the dispersibility of the scintillator particles and the particles contained in the non-scintillator layer.

Mode of Containing Transparent Fine Particles

Figure 4:
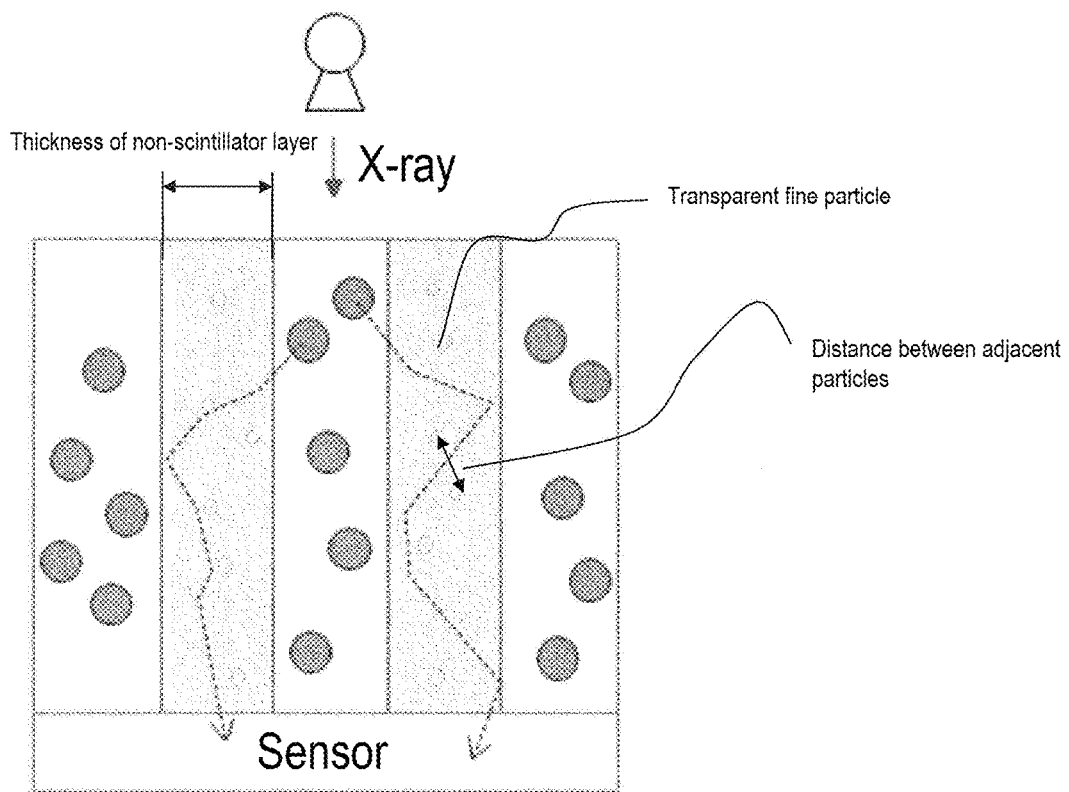
FIG. 4 is a schematic view illustrating the definition of the average gap of particles in the scintillator layer according to the present invention.

FIG. 4 illustrates a mode of containing the transparent fine particles. In this mode, the non-scintillator layer contains the transparent fine particles, and these particles exist such that their average gap is one-tenth to four times, preferably one-tenth to the same size, of the width of the non-scintillator layer.

The average gap of the particles corresponds to a mean free path (X) of light in a layer. Assuming the light collides with an object such as a filler in the non-scintillator layer, the average time between a collision and a next collision is defined as t. The average distance from the collision to the next collision is defined as mean free path X. When the light collides with a stationary object having a radius r, the geometric cross-sectional area σ is expressed as $\sigma=2\pi r^2$. The light travelling at a speed c collides with a single other object on average while travelling through the mean free path λ ($=c\tau$) with a cross-sectional area σ; therefore, the density n of the object is expressed as $n=1/(\sigma c\tau)$. Accordingly, the mean free path X is expressed as $\lambda=1/(n\sigma)$.

The average gap can be evaluated by observing a cross-sectional SEM image; however, it is also possible to calculate the average gap from the weight of the transparent fine particles dispersed in the non-scintillator layer.

In cases where the scintillator layer is formed by applying a composition containing scintillator particles and a binder resin onto a polymer film, irregularities can be generated on the surface of the resulting scintillator layer, and voids can be formed at the contact interface between the scintillator layer and the polymer film. The size of the irregularities can be arbitrarily adjusted by controlling the particle size and the dispersibility of the scintillator particles. Further, in the process of preparing the scintillator layer, air bubbles may be incorporated into the scintillator layer, or hollow polymer particles may be added. Meanwhile, even when the scintillator layer or the non-scintillator layer has irregularities on the surface, the same effects can be attained since voids are formed at contact interface of these layers.

Similarly, the transparent fine particles may be incorporated into the non-scintillator layer in a weight that is derived from the desired distance between the particles.

EFFECTS OF THE INVENTION

According to the present invention, by adjusting the refractive index values of the respective layers and the properties of the interface between layers as well as the composition of non-scintillator layer, a scintillator panel which effectively utilizes the non-scintillator layer to transmit light and has high brightness and MTF can be obtained.

Accordingly, the scintillator panel of the present invention can be used in high-voltage photographing and thus enables to capture images of thick subjects, such as thoracoabdominal parts, femoral parts, elbow joints, knee joints, and hip joints.

Conventionally, MRI is mainly used for image diagnosis of cartilages; however, there are drawbacks in that the imaging cost is high because of the use of a large-scale equipment and a long time is required for the imaging. On the other hand, according to the present invention, X-ray images of soft tissues such as cartilages, muscle tendons, and ligaments as well as visceral tissues can be obtained at a lower cost in a speedier manner. Therefore, the present invention is expected to be widely applied to image diagnosis of orthopedic diseases, such as rheumatoid arthritis and knee osteoarthritis, and soft tissues including breast cancer.

Scintillator Panel Production Method

As a method of forming a scintillator panel, a composition in which the above-described scintillator particles and adhesive resin are dissolved or dispersed in a solvent may be applied onto a non-scintillator layer to obtain a lattice-type scintillator, or may be filled into segmented partition walls to obtain a segmented scintillator.

For example, a composition prepared by heat-melting a mixture containing the above-described scintillator particles and adhesive resin is used.

In the case of preparing a composition in which the above-described scintillator particles and adhesive resin are dissolved or dispersed in a solvent, examples of a solvent that can be used include lower alcohols, such as methanol, ethanol, isopropanol, and n-butanol; ketones, such as acetone, methyl ethyl ketone, methyl isobutyl ketone, and cyclohexanone; aromatic compounds, such as toluene, benzene, cyclohexane, cyclohexanone, and xylene; esters formed by a lower fatty acid and a lower alcohol, such as methyl acetate, ethyl acetate, and n-butyl acetate; ethers, such as dioxane, ethylene glycol monoethyl ether, ethylene glycol monomethyl ether, propylene glycol monomethyl ether, and propylene glycol monomethyl ether acetate; halogenated hydrocarbons, such as benzenetriol, methylene chloride, and ethylene chloride; and mixtures thereof. In the composition, a variety of additives, such as a dispersant for improving the dispersibility of the scintillator particles in the composition, and a curing agent or a plasticizer for improving the bonding force between the adhesive resin and the scintillator particles in the resulting scintillator layer, may be mixed.

Examples of the dispersant used for such purpose include phthalic acid, stearic acid, caproic acid, and a lipophilic surfactant.

Examples of the plasticizer include phosphoric acid esters, such as triphenyl phosphate, tricresyl phosphate, and diphenyl phosphate; phthalic acid esters, such as diethyl phthalate and dimethoxyethyl phthalate; glycolic acid esters, such as ethyl phthalyl ethyl glycolate and butyl phthalyl butyl glycolate; and polyesters formed by a polyethylene glycol and an aliphatic dibasic acid, such as a polyester of triethylene glycol and adipic acid, and a polyester of diethylene glycol and succinic acid. As the curing agent, any curing agent known as a curing agent of a thermosetting resin can be used.

In the case of heat-melting and coating a mixture containing the above-described scintillator particles and adhesive resin, it is preferred to use a hot-melt resin as the adhesive resin. As the hot-melt resin, for example, resins containing a polyolefin-based, polyamide-based, polyester-based, polyurethane-based, or acrylic resin as a main component can be used. Among such resins, from the standpoints of optical transparency, moisture resistance and adhesiveness, one containing a polyolefin-based resin as a main component is preferred. As the polyolefin-based resin, for example, an ethylene-vinyl acetate copolymer (EVA), an ethylene-acrylic acid copolymer (EAA), an ethylene-acrylate copolymer (EMA), an ethylene-methacrylic acid copolymer (EMAA), an ethylene-methacrylate copolymer (EMMA), or an ionomer resin can be used. These resins may be used in the form of a so-called polymer blend in which two or more resins are combined.

Means for coating the composition for the formation of a scintillator layer is not particularly restricted, and ordinary coating means such as a doctor blade, a roll coater, a knife coater, an extrusion coater, a die coater, a gravure coater, a lip coater, a capillary coater or a bar coater, or a commonly-used method such as dipping, spraying or spinning can be employed.

When the scintillator panel of the present invention is, for example, a lattice-type scintillator, it is produced by the steps of repeatedly laminating the scintillator layer and the non-scintillator layer and subsequently bonding the thus laminated layers.

A method of repeatedly laminating the scintillator layer and the non-scintillator layer is not particularly restricted, and the scintillator layer and the non-scintillator layer that have been individually formed in advance may each be divided into plural sheets, and these sheets may be subsequently laminated alternately and repeatedly.

In the present invention, a mode of bonding together the scintillator layer and the non-scintillator layer to prepare plural partial laminates and subsequently laminating the thus obtained plural partial laminates to form the above-described laminate is preferred since it is easy to adjust the number of layers the thickness of the laminate.

A method of pressurizing the repeated laminate of the plural scintillator layers and non-scintillator layers so as to allow the repeated laminate to have desired dimensions is not particularly restricted; however, it is preferred to perform the pressurization with a spacer made of, for example, a metal being arranged in advance so that the laminate is not compressed further than the desired dimensions. The pressure applied in this process is preferably 1 MPa to 10 GPa.

When the pressure is less than the lower limit value of this range, there is a risk that a resin component contained in the laminate cannot be deformed into prescribed dimensions. When the pressure is higher than the upper limit value of this range, the spacer may be deformed, potentially causing the laminate to be compressed further than the desired dimensions. By heating the laminate in a pressurized state, the laminated layers can be more firmly bonded.

Although the conditions of heating the repeated laminate of the plural scintillator layers and non-scintillator layers vary depending on the type of a resin, it is preferred to heat the repeated laminate for about 0.5 to 24 hours at a temperature of not lower than the glass transition temperature when the resin is a thermoplastic resin, or at a temperature of not lower than the curing temperature when the resin is a thermosetting resin. Generally, the heating temperature is preferably 40° C. to 250° C. When the temperature is below the lower limit value of this range, fusion or curing reaction of the resin may be insufficient, and this potentially results in defective bonding or causes the laminate to return back to the original dimensions once the compression is released. When the temperature is above the upper limit value of this range, there is a risk that the resin is deteriorated and the optical characteristics are impaired. The method of heating the laminate under pressure is not particularly restricted, and a press machine equipped with a heating element may be used or the laminate may be oven-heated in a state of being confined in a box-shaped jig such that the resulting laminate has prescribed dimensions, or a heating element may be mounted on the box-shaped jig.

As for the state of the repeated laminate of the plural scintillator layers and non-scintillator layers prior to the pressurization, it is preferred that voids exist inside the scintillator layers, inside the non-scintillator layers, or at the interfaces between the scintillator layers and the non-scintillator layers. When the pressurization is performed in the complete absence of such voids, a constituent material may partially flow out from an end surface of the laminate to cause disruption in the lamination pitch, or may cause the laminate to return back to the original dimensions once the pressure is released. With such voids being present, the voids function as a cushion even when the laminate is pressurized, and the laminate can thus be adjusted to have arbitrary dimensions within a range where the voids are not eliminated, i.e., the lamination pitch can be adjusted to an arbitrary value. The porosity is calculated by the following formula from a measured volume of the laminate (area× thickness) and the theoretical volume of the laminate (weight/density):

(Measured volume of laminate−Theoretical volume of laminate)/Theoretical volume of laminate× 100

When the area of the laminate is constant, the porosity is calculated by the following formula from a measured thickness of the laminate and the theoretical thickness of the laminate (weight/density/area):

(Measured thickness of laminate−Theoretical thickness of laminate)/Theoretical thickness of laminate×100

The porosity of the scintillator layers after the heating is preferably 30% by volume or lower. When the porosity is higher than this range, the filling rate of the scintillator decreases, and the brightness is thus reduced.

In the present invention, when the radiation incident side of the scintillator is defined as a first surface and the side opposite to the first surface is defined as a second surface, the lamination pitch of the scintillator layers and the non-scintillator layers may be larger on the second surface than on the first surface. Specifically, the scintillator panel is curved, or has an inclined structure even without being curved (hereinafter, also referred to as "inclined scintillator"). By adopting this configuration, the problem of so-called vignetting, which is insufficient transmission of radiation caused by oblique incidence of an X-ray in the peripheral region of a scintillator, can be solved.

A segmented scintillator can be produced referring to JP 2011-21924A. In other words, a prescribed paste is applied onto a radiolucent plate-form substrate by screen-printing at a prescribed thickness and subsequently dried to form a bottom part of a partition wall structure. Then, using a lattice-shaped pattern having a size determined by the number of pixels, the above-described past composed of prescribed materials is further screen-printed in a lattice shape that has a prescribed pitch of vertical and lateral pixel units, openings of a prescribed size and a prescribed thickness, followed by drying. This operation is repeated multiple times to prepare partition walls at a prescribed height, whereby a partition wall structure, which has segments each constituted by a space separated by the bottom part and the partition walls, is formed on the substrate. Thereafter, the segments are each filled with a phosphor, as a result of which a scintillator having a segmented structure in which the partition wall structure serves as a non-scintillator layer and each segment serves as a scintillator layer is produced.

The thickness of a pair of the scintillator layer and the non-scintillator layer in a direction perpendicular to an incident direction, i.e., the thickness of the pair in the lamination direction (hereinafter, referred to as "lamination pitch"), and the thickness ratio of the scintillator layer and the non-scintillator layer in the lamination direction (hereinafter, referred to as "duty ratio") are derived from Talbot interference conditions; however, generally speaking, the lamination pitch is 0.5 to 50 µm, and the duty ratio is preferably 30/70 to 70/30. In order to acquire a diagnostic image with a sufficient area, the number of layers repeatedly laminated at such a lamination pitch is preferably 1,000 to 500,000.

In the above-described scintillator panel, as required, in order to maintain the laminated structure of the laminate, either or both of the surface on the radiation incident side and the surface on the opposite side may be pasted and thereby retained on a support. It is also possible to allow the substrate of a detector to double as the support.

As the support, a variety of glasses, polymer materials and metals that are capable of transmitting radiation such as X-rays can be used, and examples thereof include glass plates made of quartz, borosilicate glass, or chemically reinforced glass; ceramic substrates made of sapphire, silicon nitride, or silicon carbide; semiconductor substrates (photoelectric conversion panels) made of silicon, germanium, gallium arsenide, gallium phosphide, or gallium nitride; polymer films (plastic films), such as cellulose acetate films, polyester films, polyethylene terephthalate films, polyamide films, polyimide films, triacetate films, and polycarbonate films; metal sheets, such as aluminum sheets, iron sheets, and copper sheets; metal sheets having a coating layer of a metal oxide; carbon fiber-reinforced resin (CFRP) sheets; and amorphous carbon sheets. The thickness of the support is preferably 50 µm to 2,000 µm, more preferably 50 to 1,000 µm.

A method of pasting the scintillator panel to the support is not particularly specified and, for example, an adhesive, a double-sided tape, or a hot-melt sheet can be used. After the scintillator panel is pasted to the support, the surface opposite to the pasted surface may be flattened.

Between the scintillator panel and the support, a layer that reflects light emitted from the scintillator or a layer that absorbs light emitted from the scintillator may be arranged depending on the intended use. The brightness is improved by arranging a layer that reflects light emitted from the scintillator, while the sharpness is improved by arranging a layer that absorbs light emitted from the scintillator. The support itself may have a function of reflecting or absorbing light emitted from the scintillator.

Detector

In the present invention, a detector which detects light emitted from a scintillator layer upon receiving radiation is arranged on the radiation incident side of the scintillator panel.

In the detector, light converted from an incoming X-ray by the scintillator layer is converted into an electrical signal, and this electrical signal can be output to the outside in the form of being associated with positional information.

The shape of the detector is not particularly restricted as long as the detector has a function of absorbing an emitted light and converting it into the form of an electric charge, and the detector may have a planar shape, a curved shape or a corrugated shape depending on the shape of the scintillator panel.

The detector used in the present invention has a role of converting light into an electrical signal and outputting the electrical signal to the outside, and the configuration of the detector is not particularly restricted as long as a conventionally known detector can be used; however, the detector usually has a form in which a substrate, an image signal output layer and a photoelectric conversion element are laminated in this order.

Among these constituents, the photoelectric conversion element has a function of absorbing light generated by the scintillator layer and converting it into the form of an electric charge. The photoelectric conversion element may take any specific structure as long as it has such a function. For example, the photoelectric conversion element used in the present invention can be constituted by a transparent electrode, a charge generation layer that is excited by incident light to generate an electric charge, and a counter electrode. The transparent electrode, the charge generation layer and the counter electrode may all be conventionally known ones. Further, the photoelectric conversion element used in the present invention may be constituted by an appropriate photosensor, for example, plural photodiodes that are two-dimensionally arranged, or a two-dimensional photosensor such as a charge coupled device (CCD) or a complementary metal-oxide-semiconductor (CMOS). These photoelectric conversion elements transmit X-rays and thus rarely affect the light emission of the scintillator even when arranged on the irradiation side.

In order to reduce the optical loss at the interface between the detector and the scintillator panel, it is preferred that the detector and the scintillator panel be bonded with a transparent material having a refractive index of higher than 1.0 (air). A method of bonding the scintillator panel and the photoelectric conversion panel is not particularly specified and, for example, an adhesive, a double-sided tape, or a hot-melt sheet can be used.

According to the present invention, a scintillator panel which can have an increased thickness and exhibits high brightness and MTF and in which noise caused by, for example, X-ray vignetting is reduced can be obtained. Such a scintillator panel is capable of capturing a phase contrast image.

Figure 5:
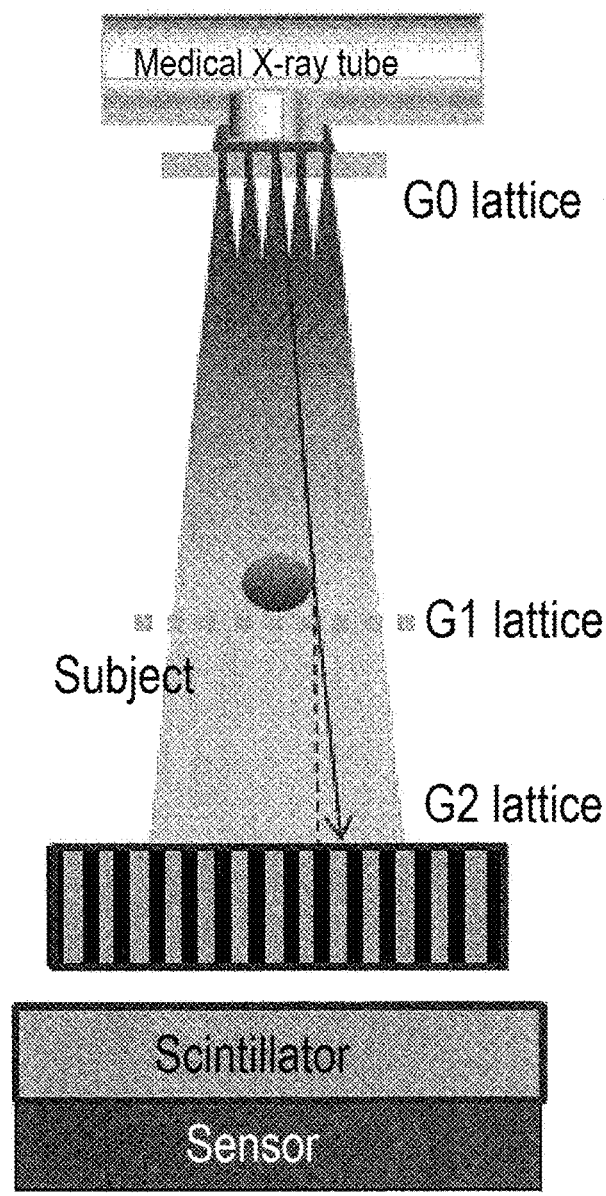
FIG. 5 is a schematic structural view of a conventional Talbot scintillator.

Therefore, the scintillator panel of the present invention can be suitably used in a Talbot system. FIG. 5 is a schematic structural view that illustrates a Talbot scintillator including the scintillator panel of the present invention.

The scintillator panel of the present invention already has the function of a G2 lattice and, therefore, can be used with a G2 lattice being removed from a device. For example, JP 2016-220865A, JP 2016-220787A, JP 2016-209017A and JP 2016-150173A provide detailed descriptions of Talbot imaging devices.

EXAMPLES

Effects of the present embodiment will now be concretely demonstrated based on the results of ray tracing simulation.

First, the basic model of the simulation will be described. A substrate, a wavelength conversion layer, a sensor protective layer and a sensor were sequentially arranged from the top and, as the wavelength conversion layer, a scintillator layer containing a phosphor and a resin and a non-scintillator layer were arranged in the form of a lattice such that they were uniformly perpendicular to the substrate and the sensor. The substrate, which was a black CFRP plate, was set in such a manner to absorb incident light. In this configuration, when viewed from the substrate side or the sensor side, the scintillator layer and the non-scintillator layer each had a short-side length of 10 μm. The phosphor, resin and air constituting the scintillator layer had a volume ratio of 50:30:20. Assuming GOS particles, the phosphor had a particle size of 2.6 μm and a refractive index of 2.3, and the resin had a refractive index of 1.52. As for the non-scintillator layer, the refractive index was set at 1.61 assuming a transparent resin such as PET. In the scintillator layer, assuming that the phosphor particles were uniformly dispersed in the resin, the diffusion of light inside the scintillator layer was set as the Mie scattering phenomenon. The sensor protective layer had a refractive index of 1.50 and a thickness of 5 μm assuming a resin such as an acrylic resin. At the interfaces of all of the members, Fresnel reflection caused by a difference in refractive index was assumed. Further, in this basic model, the thickness of the wavelength conversion layer was set at 200 μm.

In order to satisfy conditions required for the present invention, in the above-described model, convex protrusions were formed on the surface of the non-scintillator layer, and the surface roughness Ra (μm) was adjusted by modifying the shape (height and volume) and the frequency of the convex protrusions. Further, the average gap of filler particles dispersed in the non-scintillator layer was defined as S (min). In the simulation, the effects of changing Ra and S were determined.

A region of the model to be simulated was a 20-mm square region. It was assumed that an X-ray was irradiated at a tube voltage of 60 kV as an incident X-ray, and that a center position of the model region was irradiated with the X-ray having such an energy spectrum at a spot of 0.01 μm in diameter. Further, the intensity distribution of scintillation light emitted as a result of absorption of the incident X-ray was calculated by deriving the X-ray energy absorption amount, which corresponded to the penetration depth of the X-ray from the substrate surface side of the scintillator layer in the vertical direction, from the volume ratio and the mass energy absorption coefficient of the phosphor and multiplying the thus obtained value by the luminous efficiency of the phosphor.

As for the sensor serving as a light receiving surface, it was assumed that the interface between the sensor protective layer and the sensor surface did not cause optical geometric diffraction or optical scattering, and that the light receiving surface immediately absorbed the light reaching the interface.

Based on the above-described model, simulations were carried out using a ray tracing software Zemax OpticStudio manufactured by Zemax, LLC. Ten thousand rays of light corresponding to scintillation light were generated and, from the resulting point spread function (PSF) representing the intensity distribution of light absorbed by the sensor, the modulation transfer function (MTF) as an index of spatial resolution and the total absorption intensity (PSF integrated for the whole region) were determined.

As for a method of actually producing the configuration of the above-described model, PET films are coated with a paste obtained by mixing the phosphor and the resin so as to form a film thereon, and the thus obtained sheets are laminated and thermocompression-bonded to prepare a lattice-form wavelength conversion layer. Further, irregularities are formed by, for example, performing a plasma treatment on the PET film surface. The height of the irregularities is adjusted by, for example, modifying the plasma generation conditions. As for the filler contained in the non-scintillator layer, transparent fine particles are incorporated in such a manner to satisfy the above-described refractive index.

Figure 6:
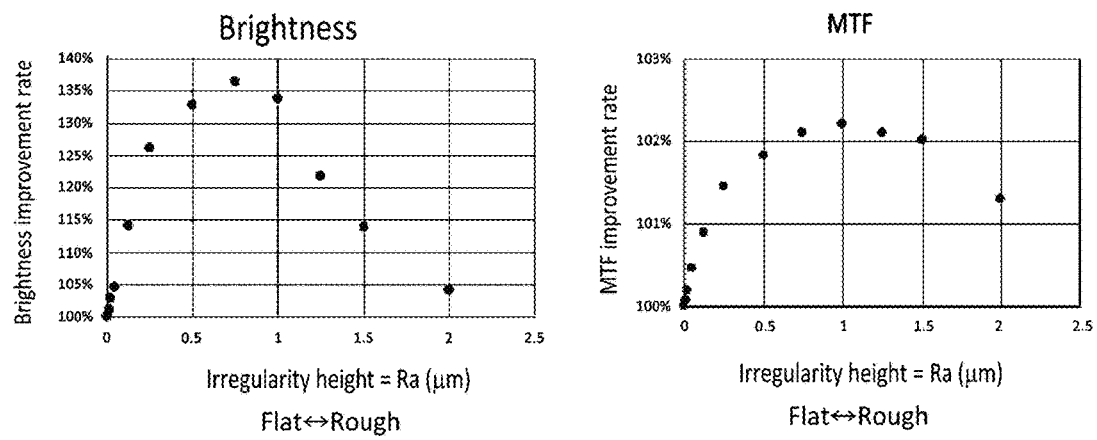
FIG. 6 shows the relationships between the brightness and the roughness and between the MTF and the roughness in Examples of a mode in which the surface roughness was defined.
Figure 7:
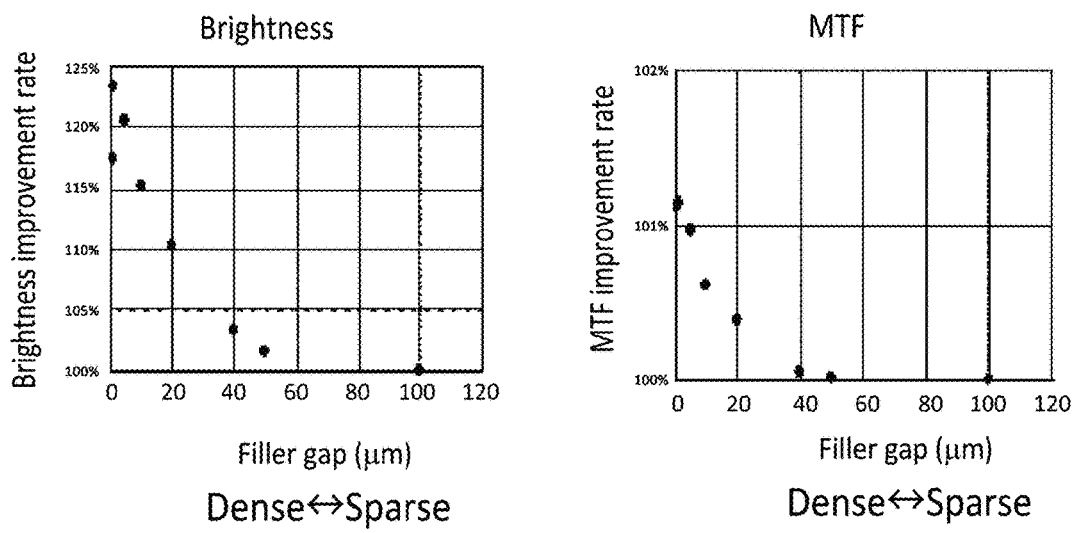
FIG. 7 shows the relationships between the brightness and the particle gap and between the MTF and the particle gap in Examples of a mode in which the average gap of particles was defined.

The evaluation results are shown in FIG. 6 and FIG. 7 and Tables 1 and 2.

From FIG. 6 and Table 1, it is seen that the brightness and the MTF increased at an interface irregularity height (=surface roughness Ra) of 0.025 μm or greater, i.e., in a range of 1/400 or greater of the non-scintillator layer width of 10 μm, while the brightness started to decrease at an irregularity height (Ra) of 1 μm, i.e., in a range of 1/10 or greater of the non-scintillator layer width, and the MTF was also in a decreasing trend in this range.

Further, with regard to the gap between particles, it is seen from FIG. 7 and Table 2 that the brightness and the MTF increased in a range where the value of the gap was 1 to 40 μm, i.e., 1/10 or greater but four times or less of the non-scintillator layer width.

In the evaluation, "○" was given to a range where the brightness and the MTF stably increased, and "-" indicates a reference evaluation result obtained for a case where the interface irregularities and the filler were not provided. Further, an evaluation of "x" was given to a range where at least either the brightness or the MTF exhibited a rapid decreasing trend associated with an increase in the amount of the interface irregularities or the filler, or a range where both the brightness and the MTF exhibited hardly any change as compared to the reference.

TABLE 1

| Surface Roughness at Interface | | | | |
| --- | --- | --- | --- | --- |
| Irregularity height = Ra (μm) | Ra/10 | Brightness | MTF | Evaluation |
| 0 | 0 | 100% | 100% | — |
| 0.0125 | 1/800 | 101% | 100% | x |
| 0.025 | 1/400 | 103% | 100% | ○ |
| 0.05 | 1/200 | 105% | 100% | ○ |
| 0.125 | 1/80 | 114% | 101% | ○ |

TABLE 1-continued

Surface Roughness at Interface

| Irregularity height = Ra (μm) | Ra/10 | Brightness | MTF | Evaluation |
|---|---|---|---|---|
| 0.25 | 1/40 | 126% | 102% | ○ |
| 0.5 | 1/20 | 133% | 102% | ○ |
| 0.75 | 1/13.3 | 136% | 102% | ○ |
| 1 | 1/10 | 134% | 102% | ○ |
| 1.25 | 1/8 | 122% | 102% | x |
| 1.5 | 1/6.7 | 114% | 102% | x |
| 2 | 1/5 | 104% | 101% | x |

TABLE 2

Filler Average Gap

| Filler average gap (μm) | S/10 | Brightness | MTF | Evaluation |
|---|---|---|---|---|
| 0.5 | 1/20 | 117% | 101% | x |
| 1 | 1/10 | 123% | 101% | ○ |
| 5 | 1/2 | 121% | 101% | ○ |
| 10 | 1 | 115% | 101% | ○ |
| 20 | 2 | 110% | 100% | ○ |
| 40 | 4 | 103% | 100% | ○ |
| 50 | 5 | 101% | 100% | x |
| 100 | 10 | 100% | 100% | x |
| no filler | — | 100% | 100% | — |

Although embodiment of the present invention has been described and illustrated in detail, it is clearly understood that the same is by way of illustration and example only and not limitation, the scope of the present invention should be interpreted by terms of the appended claims.

What is claimed is:

1. A scintillator panel having a structure in which a scintillator layer and a non-scintillator layer are repeatedly arranged in a direction substantially parallel to a radiation incident direction, wherein
    the scintillator layer comprises at least a phosphor, a binder resin, and voids,
    the non-scintillator layer is radiolucent,
    the scintillator layer and the non-scintillator layer have an irregular structure at their interface, and
    an arithmetic surface roughness Ra attributed to irregularities is 1/400 to 1/10 of the width of the non-scintillator layer.

2. The scintillator panel according to claim 1, wherein an average refractive index n1 of the binder resin and the voids of the scintillator layer and a refractive index n2 of the non-scintillator layer satisfy a relationship of n1<n2.

3. The scintillator panel according to claim 1, capturing a phase contrast image.

4. A scintillator panel having a structure in which a scintillator layer and a non-scintillator layer are repeatedly arranged in a direction substantially parallel to a radiation incident direction, wherein
    the scintillator layer comprises at least a phosphor, a binder resin, and voids,
    the non-scintillator layer is radiolucent and comprises transparent fine particles, and
    the translucent fine particles exist such that their average gap is 1/10 to four times of the width of the non-scintillator layer.

* * * * *